United States Patent [19]
Cohen et al.

[11] Patent Number: 6,165,997
[45] Date of Patent: Dec. 26, 2000

[54] PHOSPHOLIPIDS HAVING ANTIMICROBIAL ACTIVITY WITH OR WITHOUT THE PRESENCE OF ANTIMICROBIALS

[75] Inventors: Paul S. Cohen, Kingston, R.I.; Karen A. Krogfelt, Copenhagen, Denmark; David C. Laux; Maryjane Utley, both of Kingston, R.I.

[73] Assignee: Statens Serum Institut, Copenhagen, Denmark

[21] Appl. No.: 09/196,354

[22] Filed: Nov. 19, 1998

Related U.S. Application Data
[60] Provisional application No. 60/066,901, Nov. 20, 1997.

[51] Int. Cl.$^7$ ...................................................... A01N 57/10
[52] U.S. Cl. .............................. 514/148; 554/79; 554/85; 554/88; 554/96; 514/143; 514/517
[58] Field of Search .................................. 554/79, 85, 88, 554/96; 514/143, 148, 517

[56] References Cited

U.S. PATENT DOCUMENTS

| | | |
|---|---|---|
| 4,588,578 | 5/1986 | Fountain et al. . |
| 4,619,794 | 10/1986 | Hauser . |
| 4,897,384 | 1/1990 | Janoff et al. . |
| 4,923,854 | 5/1990 | Tilcock et al. . |
| 4,999,199 | 3/1991 | Anaissie et al. . |
| 5,135,922 | 8/1992 | Vitale . |
| 5,409,704 | 4/1995 | Bally et al. . |
| 5,434,182 | 7/1995 | Isaacs et al. ............................. 514/546 |
| 5,466,714 | 11/1995 | Isaacs et al. . |
| 5,478,819 | 12/1995 | Tarpila et al. . |
| 5,480,877 | 1/1996 | Mosher, Jr. ............................ 514/134 |
| 5,585,106 | 12/1996 | Gristina et al. . |
| 5,624,958 | 4/1997 | Isaacs et al. . |
| 5,648,348 | 7/1997 | Fost et al. . |

FOREIGN PATENT DOCUMENTS

| | | |
|---|---|---|
| 505817 | 2/1992 | European Pat. Off. ........ A61K 31/66 |
| 0394265 B1 | 11/1994 | European Pat. Off. . |
| 719543 | 7/1996 | European Pat. Off. ......... A61K 7/48 |
| 0282405 B2 | 7/1998 | European Pat. Off. . |
| 740028230 | 3/1974 | Japan . |
| 770033139 | 3/1977 | Japan . |
| 850055564 | 7/1985 | Japan . |
| 930320885 | 11/1993 | Japan . |
| 9211015 | 7/1992 | WIPO . |
| WO 93/08807 | 5/1993 | WIPO . |
| WO 93/09805 | 5/1993 | WIPO . |
| WO95/32716 | 12/1995 | WIPO . |

OTHER PUBLICATIONS

Chem. Abstr., vol. 108, abstr. 200731, Gonzales et al., 1988.

John Pace et al., "Singal Transduction and Invasion of Epithelial Cells by *S. typhimurium*", Cell, vol. 72 (Feb. 26, 1993) pp. 505–514.

Barbara L. Angus, et al., "Outer Membrane Permeability in *Pseudomonas aeruginosa*: Comparison of a Wild–type with an Antibiotic–Supersusceptible Mutant", Antimicrobial Agents and Chemotherapy, vol. 21, No. 2 (Feb. 1982) pp. 299–309.

Hans G. Boman, "Antibacterial Peptides: Key Components Needed in Immunity", Cell, vol. 65 (Apr. 19, 1991) pp. 205–207.

Hans G. Boman, et al., "Cell–free immunity in Cecropia. A model system for antibacterial proteins" Eur. J. Biochem, vol. 201 (Feb. 1991) pp. 23–31.

Deb K. Chatterjee et al., "Genetic Rearrangements in Plasmids Specifying Total Degradation of Chlorinated Benzoic Acids", Mol. Gen. Genet., vol. 188 (1982) pp. 279–285.

P.S. Chen, et al., "Microdetermination of Phosphorus", Analytical Chemistry, vol. 28, No. 11 (Nov. 1956) pp. 1756–1758.

Peter Elsbach et al., "Separation and Purification of a Potent Bactericidal/Permeability–increasing Protein and a Closely Associated Phospholipase A2 from Rabbit Polymorphonuclear Leukocytes", Journal of Biological Chemistry, vol. 254, No. 21 (Nov. 10, 1979) pp. 11000–11009.

Birgit Giwereman et al., "Rapid emergence of resistance in *Pseudomonas aeruginosa* in cystic fibrosis patients due to in–vivo selection of stable partially derepressed B–lactamase producing strains", Journal of Antimicrobial Chemotherapy, vol. 26 (1990) pp. 247–259.

J.R.W. Govan et al., "Microbial Pathogenesis in Cystic Fibrosis: Mucoid *Pseudomonas aeruginosa* and *Burkholderia cepacia*" Microbioligical Reviews, vol. 60, No. 3 (Sep. 1996) pp. 539–574.

Robert E.W. Hancock, "The bacterical outer membrane as a drug barrier", Trends in Microbiology, vol. 5, No. 1 (Jan. 1997) pp. 37–42.

Robert E.W. Hancock, et al., "Outer Membrane on *Pseudomonas aeruginosa*: Heat– and 2–Mercaptoethanol–Modifiable Proteins", Journal of Bacteriology, vol. 140, No. 3 (Dec. 1979) pp. 902–910.

Robert E.W. Hancock et al., "*Pseudomonas aeruginosa* Isolates from Patients with Cystic Fibrosis: A Class of Serum–Sensitive, Nontypable Strains Deficient in Lipoposaccharide O Side Chains", Infection and Immunity, vol. 42, No. 1 (1983) pp. 170–177.

Robert E.W. Hancock, et al., "Involvment of the Outer Membrane in Gentamicin and Streptomycin Uptake and Killing in *Pseudomonas aeruginosa*", Antimicrobial Agents and Chemotherapy, vol. 19, No. 5 (May 1981) pp. 777–785.

Robert E.W. Hancock, et al., "Compounds Which Increase the Permeability of the *Pseudomonas aeruginosa* Outer Membrane", Antimicrobial Agents and Chemotherapy, vol. 26, No. 1 (Jul. 1984) pp. 48–52.

Robert I. Lehrer et al., "Antimicrobial Polypeptides of Human Neutrophils", Blood: Journal of The American Society of Hematology, vol. 76, No. 11 (Dec. 1990) pp. 2169–2181.

(List continued on next page.)

*Primary Examiner*—Deborah D. Carr
*Attorney, Agent, or Firm*—Birch, Stewart, Kolasch & Birch, LLP

[57] ABSTRACT

A pharmaceutical formulation for stimulating growth of Gram-positive Bacilli and increasing the acidity in vagina comprises sucrose and/or maltose, optionally with other sugars, viscous base, and anti-fungal and/or anti-bacterial agents.

15 Claims, No Drawings

OTHER PUBLICATIONS

Robert I. Lehrer et al., "Defensins: Endogenous Antibiotic Peptides of Animal Cells", Cell, vol. 64 (Jan. 1991) pp. 229–230.

D.M. Livermore, "Clinical Significance of Beta–Lactamase Induction and Stable Derepression in Gram–Negative Rods", Eur. J. Clin. Microbiol, vol. 6, No. 4 (Aug. 1987) pp. 439–445.

B. Ojeniyi et al., "Prevalence and persistence of polyagglutinable *Pseudomonas aeruginosa* in isolates from cystic fibrosis patients", APMIS, vol. 99 (1991) pp. 187–195.

Svend Stenvang Pedersen et al., "*Pseudomonas aeruginosa*Alginate in Cystic Fibrosis Sputum and the Inflammatory Response", Infection and Immunity, vol. 58, No. 10 (Oct. 1990) pp.3363–3368.

Keith Poole et al., "Overexpression of the mexC–mexD–oprJ efflux operon in nfxB–type multidrug–resistant strains of *Pseudomonas aeruginosa*", Molecular Microbiology, vol. 21, No. 4 (1996) pp. 713–724.

Keith Poole et al., "Espression of the Multidrug Resistance Operon mexA–mexB–oprM in *Pseudomonas aeruginosa*: mexR Encodes a Regulator of Operon Expression", Antimicrobial Agents and Chemotherapy, vol. 40, No. 9 (Sep. 1996) pp. 2021–2028.

M.H. Richmond et al., "The B–Lactamases of Gram–Negative Bacteria and their Possible Physiological Role", Adv. Microbiol Physiol., vol. 9 (1973) pp. 31–88.

R.B. Sykes et al., "Resistance of *Pseudomonas aeruginosa* to Antimicrobial Drugs", Progress in Medicinal Chemistry, vol. 12 (1975) pp. 333–393.

Martti Vaara, "Agents That Increase the Permeability of the Outer Membrane", vol. 56, No. 3 (Sep. 1992) pp. 395–411.

Martti Vaara et al., "Polycations Sensitize Enteric Bacteria to Antibiotics", Antimicrobial Agents and Chemotherapy, vol. 24, No. 1 (Jul. 1983) pp. 107–113.

Petri Viljanen et al., "The Outer Membrane Permeability--Increasing Action of Deacylpolymyxins", The Journal of Antibiotics, vol. 44, No. 5 (May 1991) pp. 517–523.

Wendy A. Woodruff et al., "Construction and Characterization of *Pseudomonas aeruginosa* Protein F–Deficient Mutants after In Vitro and In Vivo Insertion Mutagenesis of the Cloned Gene", Journal of Bacteriology, vol. 170, No. 6 (Jun. 1988) pp. 2592–2598.

Fuminobu Yoshimura et al., Permeability of *Pseudomonas aeruginosa* Outer Membrane to Hydrophilic Solutes', Journal of Bacteriology, vol. 152, No. 2 (Nov. 1982) pp. 636–642.

Xin Zhou et al., "Isolation and Characterization of an Attenuated Strain of *Pseudomonas aeruginosa* AC869, a 3,5–Dichlorobenzoate Degrader", Applied and Environmental Microbiology, vol. 63, No. 4 (Apr. 1997) pp. 1389–1395.

Carl I. Price et al., "Liposome encapsulation: A method of enhancing the effectiveness of local antibiotics", Surgery, vol. 115, No. 4 (Apr. 1994) pp. 480–487.

Jacqueline Lagage et al., "Liposome–encapsulated antibiotics: preparation, drug release and antimicrobial activity against *Pseudomonas aeruginosa*", J. Microencapsulation, vol. 8, Nol. 1 (1991) pp. 53–61.

Hiroshi Nikaido, "Outer Membrane", *Escherichia coli* and Salmonella—Cellular and Molecular Biology, vol. 1, 2nd Ed. (19 ) pp. 29–47.

O. Ciofu et al., "Development of antibiotic resistance in *Pseudomonas aeruginosa* during two decades of antipseudomonal treatment at the Danish CF Center", APMIS, vol. 102 (1994) pp. 674–680.

Helen R. Revel, "Restriction of Nonglucosylated T–even Bacteriophage: Properties of Permissive Mutants of *Escherichia coli* B and K12", Virology, vol. 31 (1967) pp. 688–701.

Douglas S. Kernodle et al., "Comparative Prophylactic Efficacies of Ciproflosacin, Ofloxacin, Cefazolin, and Vancomycin in Experimental Model of Staphylococcal Wound Infection", Antimicrobial Agents and Chemotherapy, vol. 38, No. 6 (Jun. 1994) pp. 1325–1330.

Michael J. Preston et al., "Rapid and Sensitive Method for Evaluating *Pseudomonas aeruginosa* Virulence Factors during Corneal Infections in Mice", Infection and Immunity, vol. 63, No. 9 (Sep. 1995) pp. 3497–3501.

PHOSPHOLIPIDS HAVING ANTIMICROBIAL ACTIVITY WITH OR WITHOUT THE PRESENCE OF ANTIMICROBIALS

This application claims priority on provisional application Ser. No. 60/066,901 filed on Nov. 20, 1997, the entire contents of which are hereby incorporated by reference.

BACKGROUND OF THE INVENTION

During the last decades a dramatic increase in bacterial strains multiresistant to antibiotics has been reported. This increase has led to the occurrence of incurable bacterial infections with a fatal outcome, and a particularly serious problem in connection with hospital-acquired infections. The emergence of antibiotic resistance is a result of the overwhelming use of antibiotics in human and veterinary medicine. Furthermore, the incidence of allergy towards the presently most effective antimicrobials further complicates the treatment of bacterial infections.

It is generally believed that if the bacterial membrane could only be permeabilized, the effect of antibiotics would be enhanced. A great deal of effort has gone into attempts to permeabilize the Gram negative outer membrane to antibiotics in the hope that some permeabilizers may prove clinically useful. Several polycations have been shown to permeabilize the outer membrane, presumably by binding to lipopolysaccharide (LPS). Among the polycation permeabilizers are polymixin B and its derivatives (Vaara, M., and Vaara, T., 1983), including deacylpolymixin B and polymixin B nonapeptide (Viljanen, P. H. et al., 1991). Other polycationic permeabilizers include bactericidal/permeability-increasing protein, protamine, and various polycationic peptides including lysine polymers, defensins, cecropins, magainins, and mellitin. Chelators, such as ethylenediaminetetraacetate (EDTA), nitrilotriacetate, and sodium hexametaphosphate have proved to be effective outer membrane permeabilizers. Chelators presumably permeabilize by removing calcium and magnesium ions from LPS, resulting in release of much of the LPS from the outer membrane and consequent outer membrane destabilisation.

SUMMARY OF THE INVENTION

The substances described in the present application are phospholipids that not only markedly enhance the effect of an antimicrobial but also by themselves have antimicrobial activity. The substances are presently contemplated not to cause problems of resistance. Furthermore, the substances are non-toxic since phospholipids are naturally found in the host, i.e. in mucosal surfaces and in the bloodstream. Thus, the substances are presently contemplated not to cause problems with regard to allergy. Phospholipids are used as carriers of various medically active substances and serve either as vesicles for the slow release of, e.g., an antibiotic, or as coating agents for protecting an active substance from, e.g., acid degradation in the stomach. This is the first time that phospholipids have been used as antimicrobials or as enhancers of antimicrobial activity.

DETAILED DISCLOSURE

The present invention relates to, inter alia, a surprising antimicrobial effect and a surprising enhancing effect of the antimicrobial activity of a traditional antimicrobial. The substance of the invention has the general formula (I):

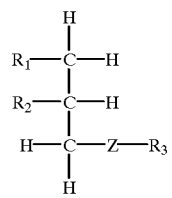

In the general formula (I), C and H have their normal meaning, i.e. carbon and hydrogen atoms respectively, and Z represents a phosphorus or sulfur oxyacid residue, such as:

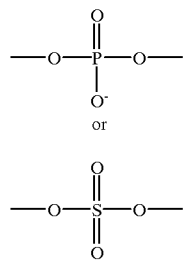

In the general formula (I), $R_1$ and $R_2$ independently represent a hydroxy group (—OH), or an alkyl group, an alkoxy group, or a saturated or ethylenically unsaturated fatty acid residue with at least 7 carbon atoms. Examples of appropriate naturally occurring saturated fatty acid residues are residues derived from octanoic, decanoic, dodecanoic, tetradecanoic, hexadecanoic, octadecanoic, eicosanoic, docosanoic, tetracosanoic, and hexacosanoic acid, and examples of appropriate naturally occurring unsaturated fatty acid residues are residues derived from hexadec-9-enoic, octadec-9-enoic, octadec-11-enoic, octadeca-9,12-dienoic, octadeca-9,11,13-trienoic, octadeca-9,12,15-trienoic, octadeca-6,9,12,15-tetraenoic acid, and eicosa-5,8,11,14-tetraenoic acid including cis and trans isomeric forms thereof with respect to the ethylenic double bounds. Also, substances of formula (I) containing fatty acid residues with an uneven number of carbon atoms or fatty acid residues with side chains, e.g. residues derived from 3,7,11,15-tetramethylhexadecanoic acid, are anticipated to have antimicrobial activity.

Preferred fatty acid residues are saturated fatty acid residues with more than 7 carbon atoms, such as between 10 and 20, more preferably 12, 13, 14, 15, or 16 carbon atoms. When one of $R_1$ or $R_2$ is a hydroxy group, the other of $R_1$ and $R_2$ should preferably be a group other than a hydroxy group, such as an alkyl group, an alkoxy group or a fatty acid residue of the above mentioned type. When one or both of $R_1$ and $R_2$ are an alkyl group or an alkoxy group, the carbon chain moiety of the group in question may suitably correspond to the carbon chain moiety of a fatty acid residue of one of the above mentioned types.

In the general formula (I), $R_3$ is a hydrogen or an uncharged or negatively charged group derived from a hydroxy-containing compound by removal of the hydroxy group. Suitable hydroxy-containing compounds include: certain amino acids, e.g. serine; ethanolamine; and certain polyols, e.g. glycerol and inositol. A neutral or negative charge on the group $R_3$ appears to be important with respect to the effect of a substance with the general formula (I)

against Gram negative bacteria and/or with respect to the enhancing effect of a substance with the general formula (I) on the activity of an antimicrobial against Gram negative bacteria.

In one aspect of the present invention, $R_3$ represents an uncharged, negatively charged or positively charged group derived from a hydroxy-containing compound by removal of the hydroxy group. An example of a suitable hydroxy-containing compound with an overall positive charge is choline.

By the term an overall neutral charge is understood that the number of positive and negative charges on the hydroxy-containing compound at physiological pH are the same. By the term an overall positive charge is understood that the number of positive charges are higher than the number of negative charges on the hydroxy-containing compound at physiological pH. By the term an overall negative charge is understood that the number of positive charges are less than the number of negative charges on the hydroxy-containing compound at physiological pH. By physiological pH is meant a pH that is between 7 and 8, such as 7.4.

By antimicrobial is understood any agent or combination of agents used in the combat of infectious diseases. That includes, but is not limited to, antifungal, antiviral, antiprotozoal, and antimicrobial drugs.

By the term "a substance of the present invention without an antimicrobial" is understood at least one substance with the general formula (I). More than one substance of the invention such as 2, 3, 4, 5, 6, 7, 8, 9 or 10 or even more different substances may be present.

By the term "a substance of the present invention with an antimicrobial" is understood at least one substance with the general formula (I) combined with at least one antimicrobial. More than one substance of the invention such as 2, 3, 4, 5, 6, 7, 8, 9 or 10 or even more different substances of the invention and more than one antimicrobial such as 2, 3, 4, 5, 6, 7, 8, 9, 10 or even more different antimicrobials may be present. Any kind of combination described above is within the scope of the invention.

By the combat of infectious disease is understood treatment, prophylaxis, cytocidal, antibacterial, bacteriostatic, and/or bacteriocidal effects.

By an antimicrobial effect of a substance is understood that the addition of the substance to a culture medium inhibits growth of the inoculum such that the colony forming unit (cfu) with the substance is less than 30%, such as 20%, 15%, 10%, or 5% of the cfu without addition of the substance. Preferably the addition of the substance kills the inoculum such that the cfu is less than 70%, such as 60%, 50%, 40%, 30%, 20%, 10%, 5%, 2%, 1%, 0.1%, or 0.01% of the inoculum.

By an enhanced effect of an antimicrobial is understood that the minimum inhibitory concentration (MIC) of the antimicrobial without the substance of the present invention is decreased by at least 10-fold by the addition of a substance of the present invention. Preferably, the decrease is at least 50-fold, such as 100-fold, 500-fold or even 1000-fold This is also referred to as a synergistic effect between the antimicrobial and the substance.

Gram positive and Gram negative bacteria are differentiated by the Gram stain. A Gram positive bacterium retains the primary stain (crystal violet) when treated with a decolourising agent (alcohol or acetone) whereas a Gram negative bacterium loses the primary stain. The staining difference reflects the structural differences in the cell walls of Gram negative and Gram positive bacteria. The Gram positive cell wall consists of a relatively thick peptidoglycan layer and teichoic acids whereas the Gram negative cell wall consists of a relatively thin peptidoglycan layer, and an outer membrane consisting of a lipid bilayer containing phospholipids, lipopolysaccharide, lipoproteins and proteins.

In one aspect of the invention, the substance enhances the effect of antimicrobials. In a second aspect of the invention, the substance has antimicrobial activity in itself, i.e. without the presence of an antimicrobial.

Some substances of relevance in relation to the present invention, such as MPPA (monopalmitoyl-phosphatidic acid) and DPPS (dipalmitoylphosphatidylserine), occur naturally. Phospholipids consist of a glycerol backbone with a phosphate group substituted for the hydroxyl group on the C3 atom (phosphoglycerides), and with fatty acids substituted for the hydroxy groups on the C1, or C2, or C1 and C2 carbon atoms. Any of a number of head groups or hydroxy-containing compounds (e.g. serine, choline, inositol, ethanolamine) can be esterified to the phosphoric acid moiety. Phospholipids can be degraded by bacteria as sources of carbon, nitrogen, and phosphate (Krivan, H. C. et al, 1992). Phospholipids occur naturally in both procaryotic and eucaryotic cell membranes. It is presently contemplated by the inventors of the present application that the production of lysophospholipids (phopholipids containing only one fatty acid) may be one of nature's ways of weakening or killing invading bacteria. For example, it is known that contact of Henle-407 epithelial cells with *Salmonella typhimurium* results in the activation of phospholipase A2 in the Henle-407 cells (Pace et al, 1993). Phospholipase A2 could generate lysophospholipids from its Henle-407 cell membranes that are damaged as *S. typhimurium* infects. The lysophopholipids could then chelate calcium and magnesium from Gram negative bacterial cells and thereby weaken them or directly kill Gram positive cells as observed in the examples presented in the following.

The present invention relates both to an antimicrobial effect and an enhancing effect of a traditional antimicrobial by a substance as described above having low, or no, toxicity. Furthermore, the substances of the invention are not likely to be immunogenic as there have not been described any allergic reactions to lipids. The usage of the substances of the invention will avoid or decrease the emergence of antibiotic resistant strains of bacteria. Thus, the applications of the present invention are numerous. Based on the findings described in the examples, it is suggested to use a substance with the general formula (I) as a medicament either alone or in connection with an antimicrobial. The substance of the present invention with or without an antimicrobial will be included in a pharmaceutical preparation and be used in medicine.

One aspect of the invention relates to the antimicrobial effect of a substance as described above alone or the synergistic effect with an antimicrobial for combating infectious diseases, in particular infections caused by microorganisms such as fungal, yeast, viral, protozoal and bacterial infections.

The substance of the present invention with or without an antimicrobial can be used for the manufacture of a medicament for the treatment of an animal with an infection caused by a spirochete. The spirochetes could be Borrelia, Leptospira or Treponema.

The substance of the present invention with or without an antimicrobial can be used for the manufacture of a medicament for the treatment of an animal with infection caused by protozoa. The protozoa could be *Entamoeba histolytica, Pneumocystic carinii, Giardia intestinalis, Trichomonas vaginalis*, Leishmania, Trypanosoma, *Isospora gondii*, or Plasmodium.

In the present examples, *Pseudomonas aeruginosa* was used as a model organism to show the effect of phospholipids. *Pseudomonas aeruginosa* is intrinsically resistant to many antibiotics. Part of this resistance can be attributed to the relatively low permeability of the *P. aeruginosa* outer membrane to a variety of antibiotics. Another part of the resistance appears to be caused by two recently discovered multidrug efflux systems. In addition, in some cases, enzymes that specifically inactivate antibiotics lead to antibiotic resistance, e.g. the inducible β-lactamase of *P. aeruginosa*. Thus, the substance can be used for the manufacture of a medicament for the treatment of an animal with an infection caused by Gram negative bacteria together with or without the presence of an antimicrobial. The Gram negative bacteria could be cocci, such as Neisseria (e.g. *N. meningitis, N. gonorrhoeae*), and Acinetobacter or rods, such as Bacteroides (e.g. *B. fragilis*), Bordetella (e.g. *B. pertussis, B. parapertussis*), Brucella (e.g. *B. melitentis, B. abortus* Bang, *B. suis*), Campylobacter (e.g. *C. jejuni, C. coli, C. fetus*), Citrobacter, Enterobacter, Escherichia (e.g. *E. coli*), Haemophilus (e.g. *H. influenzae, H. para-influenzae*), Klebsiella (e.g. *K. pneumoniae*), Legionella (e.g. *L. pneumophila*), Pasteurella (e.g. *P. yersinia, P. multocida*), Proteus (e.g. *P. mirabilis, P. vulgaris*), Pseudomonas (e.g. *P. aeruginosa, P. pseudomallei, P. mallei*), Salmonella (e.g. *S. enteritidis, S. infantits, S. Dublin S. typhi, S. paratyphi, S. schottmülleri, S. choleraesuis, S. typhimurium*, or any of their 2.500 other serotypes), Serratia (e.g. *S. marscences, S.liquifaciens*), Shigella (e.g. *S. sonnei, S. flexneri, S. dysenteriae, S. boydii*), Vibrio (e.g. *V. cholerae, V. el tor*), and Yersinia (e.g. *Y. enterocolitica, Y. pseudotuberculosis, Y. pestis*).

In a preferred embodiment, the substance with or without the presence of an antimicrobial is used for the manufacture of a medicament for the treatment of an animal being infected with Enterobacteriaceae such as *Pseudomonas aeruginosa, Salmonela enteritidis*, and *Klebsiella pneumonia*.

As seen in example 1 (tables 3 and 4) even the strains producing β-lactamase, thus resistant to a number of antibiotics, are being killed in the presence of DPPS. In case of Klebsiella, the medical threat is caused by strains producing β-lactamase therefore being resistant to antibiotics. Therefore, it is believed that other bacterial strains, cf. the above mentioned, would also be killed in the presence of the substance of the invention.

The substance can be used for the manufacture of a medicament for the treatment of an animal with infection caused by Gram positive bacteria together with or without the presence of an antimicrobial. The Gram positive bacteria could be cocci, such as Streptococcus (e.g. *S. pneumoniae, S. viridans, S. faecalis, S. pyogenes*), Staphylococcus (e.g. *S. aureus, S. epidermidis, S. saprophyticus*), and rods, such as Actinomyces (e.g. *A. israelli*), Bacillus (e.g. *B. cereus, B. subtilis, B. anthracis*), Clostridium (e.g. *C. botulinum, C. tetani, C. perfringens, C. difficile*), Corynebacterium (e.g. *C. diphtheriae*), Listeria, and Providencia. In a preferred embodiment the substance with or without the presence of an antimicrobial is used for the manufacture of a medicament for the treatment of an animal with infection caused by Staphylococcus and Enterococcus, such as *Staphylococcus aureus*.

The substance with or without the presence of an antimicrobial can be used for the manufacture of a medicament for the treatment of an animal with infection caused by Mycoplasma, *Chlamydia trachomatis, Chlamydia psittaci*, and Rickettsiae.

In the examples, scientific evidence for the mechanism by which the substance of the present invention enhances ampicillin activity against *P. aeruginosa* is disclosed. MPPA binds both magnesium and calcium, thereby reducing the calcium and magnesium concentrations with as much as 4 to 5-fold (Tables 21 and 22). Addition of calcium to MPPA supernatants completely reversed the enhancement of ampicillin activity whereas addition of magnesium did not (Tables 19 and 20) indicating that the binding of calcium is the most important. In further support that enhancement is due to MPPA binding of calcium is the finding that a higher concentration of MPPA enhanced ampicillin activity against *P. aeruginosa* PAO1 even when the concentration of calcium in L-broth was increased (Table 19). Without being bound by this theory, it is contemplated that MPPA takes calcium and magnesium from the lipopolysaccharide (LPS) of the outer membrane causing a release of LPS, thereby destabilising the membrane and permeabilizing it e.g. to an antimicrobial.

A presently preferred antimicrobial to be used in combination with the substance should be an antimicrobial that has an antimicrobial action through inhibition of cell wall synthesis, such as β-lactams and vancomycin, preferably penicillins, such as amdinocillin, ampicillin, amoxicillin, azlocillin, bacampicillin, benzathine pinicillin G, carbenicillin, cloxacillin, cyclacillin, dicloxacillin, methicillin, mezlocillin, nafcillin, oxacillin, penicillin G, penicillin V, piperacillin, and ticarcillin; cephalosporins, such as the first generation drugs cefadroxil, cefazolin, cephalexin, cephalothin, cephapirin, and cephradine, the second generation drugs cefaclor, cefamandole, cefonicid, ceforanide, cefoxitin, and cefuroxime, or the third generation cephalosprins cefoperazone, cefotaxime, cefotetan, ceftazidime, ceftizoxime, ceftriaxone, and moxalactam; carbapenems such as imipenem; or monobactams such as aztreonam.

Tetracycline resistance is in many bacteria caused by a decreased permeability of the tetracycline into the bacteria. As the membrane gets permeable by the presence of the substance of the present invention, the effect of tetracyclines could be expected to be enhanced due to the increased permeability to tetracyclines caused by changed permeability to the drug. Other antimicrobial drugs with action through inhibition of protein synthesis, such as chloramphenicol; other tetracyclines preferably demeclocycline, doxycycline, methacycline, minocycline, and oxytetracycline; aminoglycosides such as amikacin, gentamicin, kanamycin, neomycin, netilmicin, paromomycin, spectinomycin, streptomycin, and tobramycin; polymyxins such as colistin, colistimathate, and polymyxin B, and erythromycins and lincomycins are also expected to have enhanced activity in the presence of the substance of the present invention.

Antimicrobials with action through inhibition of nucleic acid synthesis in particular sulfonamides such as sulfacytine, sulfadiazine, sulfisoxazole, sulfamethoxazole, sulfamethizole, and sulfapyridine; trimethoprim, quinolones, novobiocin, pyrimethamine, and rifampin, are expected to have enhanced activity in the presence of the substance of the present invention.

Tables 15, 17, and 18 show that both MPPA and MPPC (monopalmitoylphosphatidylcholine) have activity against the Gram positive bacteria, but Table 7 shows that although MPPA has activity against *P. aeruginosa* PAO1, MPPC does not. If the action of the substance on Gram negative bacteria is in binding calcium and magnesium, it would not be expected that MPPC would work since it should not be able to bind these cations. However, MPPC does work on Gram positive bacteria and does not bind the cations. Therefore, since the mechanism of activity of MPPA on Gram positive bacteria is likely to be similar to that of MPPC, it is very likely that unlike its activity against Gram negative bacteria, the activity of MPPA on Gram positive bacteria is due to something else than the binding of calcium and magnesium. The exact mechanism is not known, but it is known that lipids bind to membranes by being inserted and integrating in the membranes, thereby destabilising the membrane. It was suggested for LPS destroying the erythrocytes.

Antimicrobials specially preferred against fungal infections include amphotericin B, flucytosine, and ketoconazole. Antimicrobials specially preferred against viral infections are acyclovir, amantadine, azidothymidine, ribavirin, and vidarabine.

In one embodiment of the present invention, a composition comprising the substance of the present invention with or without an antimicrobial is prepared as a paste. This requires addition of various substances for the final paste formulation, well known to a person skilled in the art (see, e.g., "Remington's Pharmaceutical Sciences" and "Encyclopedia of Pharmaceutical Technology"). The paste will be suitable for topical application of the antimicrobial composition for the combat of diseases such as wound burns, ulcus curis, acne, gonorrhoea (including urethritis, endocervicitis and proctitis), anthrax, tetanus, gas gangrene, scarlatina, erysipelas, sycosis barbae, folliculitis, impetigo contagiosa, or impetigo bullosa.

In another embodiment of the present invention, a composition comprising the substance of the present invention with or without an antimicrobial is prepared as a liquid. This requires addition of various substances for the final liquid formulation, well known to a person skilled in the art (see, e.g., "Remington's Pharmaceutical Sciences" and "Encyclopedia of Pharmaceutical Technology"). The liquid will be suitable for injection into the infected area or application onto the infected area for the combat of diseases such as eye infections (orbital cellulitis, conjunctivitis), periodontitis, otitis (otitis media, sinuitis), mouth infections, throat infections, or anthrax.

In yet another embodiment of the present invention, a composition comprising the substance of the present invention with or without an antimicrobial is prepared as a vapour. This requires addition of various substances for the final vapour formulation, well known to a person skilled in the art (see, e.g., "Remington's Pharmaceutical Sciences" and "Encyclopedia of Pharmaceutical Technology"). The vapour will be suitable for the inhalation, e.g. through the nose or the mouth, of the antimicrobial composition, for the combat of diseases such as lung infections (such as pneumonia and cystic fibrosis), diphtheria, pertussis (whopping cough), epiglottitis, nasopharyngitis, bronchitis, and tonsillitis.

In one embodiment of the present invention, a composition comprising the substance of the present invention with or without an antimicrobial is prepared as a liquid or solid. This requires addition of various substances for the final liquid or soluble formulation, well known to a person skilled in the art (see, e.g., "Remington's Pharmaceutical Sciences" and "Encyclopedia of Pharmaceutical Technology"). The liquid or solid will be suitable for the oral administration of the antimicrobial composition for the combat of diseases such as gastritis, typhus, gastroenteritis, anthrax, botulism, pseudomembranous colitis, dysentery, enterocolitis, peritonitis, abscess, pertussis, cholera, pestis, cystitis, pneumonia, meningitis, and Crohn's disease.

Many diseases arise from a primary infection with any bacterium, but is caused by the secondary spread of the infectious agent from the primary infection site. Thus, usage of a composition of the substance of the invention with or without an antimicrobial will be useful for the prophylaxis of disease, i.e. for the manufacture of a medicament for the prophylaxis of disease, such as any of the diseases mentioned above.

In a preferred embodiment of the invention, the substance of the present invention with or without the presence of an antimicrobial combat or prevent infection in any animal preferably a mammal such as a pet, e.g. cat, dog, or guinea pig; or a zoo animal. In further preferred embodiments, the animal is part of the industry, preferably a farm animal such as cattle, a horse, pig, mink, goat, or sheep, or a bird, such as chicken, ostrich, turkey, duck, or goose. In the most preferred embodiment, the mammal is a human being.

In yet another embodiment of the invention, the substance of the invention with or without the presence of an antimicrobial is administrered perorally, parenterally, intravenously, topically, vaginally, or rectally as active ingredient in customary pharmaceutical compositions.

One important aspect of the invention is a pharmaceutical composition comprising the substance of the invention with or without an antimicrobial. In order to obtain registration for human use, several steps have to be carried out.

The first step will be testing the substance of the invention with or without an antimicrobial in animal models. As one example, the substance of the invention with or without the presence of an antimicrobial is tested in the cystic fibrosis rat model described by Cash et al. 1979. *P. aeruginosa* strains 17107 and 19676 have been used in the rat model, as they are able to induce a chronic inflammation of the lung. As MPPA has effect against strains 17107 and 19676 in vitro, it is contemplated that it will have effect in the model as well. Skin burn models are widely used (Kernodle and Kaiser, 1994) where the effect against infections with Gram positive and Gram negative bacteria can be tested. Other animal models for infectious diseases will be known to a person skilled in the art. In each of these models, it is contemplated that a structure-activity relationship experiment as described in Example 1 will be necessary. Local metabolism, diffusion, interference with biological balance, penetration, and solubility are just a few factors that will affect the transition from in vitro to in vivo data.

The second step will be exploration of the toxicity of the substance of the invention with or without the presence of an antimicrobial. These studies will be carried out in models as required by the medical evaluation agencies. It is anticipated that the toxicity of the substance of the invention is low.

The third step will be formulation of the substance of the invention with or without the presence of an antimicrobial. In one aspect of the formulation, it is formulated as a preparation for topical administration as a pharmaceutical cosmetic composition or a skin care composition comprising the substance of the invention with or without the presence of an antimicrobial. Pharmaceutical, cosmetic and skin care compositions of the invention suitable for topical administration may be creams, ointments, lotions, liniments, gels, solutions, suspensions, pastes, sticks, sprays, shampoos, soaps, hair conditioners or powders.

The topical administration may be an administration onto or close to the parts of the body presenting the infection, e.g. onto an exterior part of the body such as a skin surface. The application may be a simple smearing on of the composition, or it may involve any device suited for enhancing the establishment of contact between the composition and the infection site such as the use of occlusive dressings, e.g. occlusion plasters provided with the composition of the invention. The compositions may be impregnated or distributed onto pads, plasters, strips, gauze, sponge materials, cotton wool pieces, etc. Optionally, a form of injection of the composition into or near the lesions may be employed.

The topical compositions according to the present invention may comprise 0.001–80% of the active substance with or without the presence of an antimicrobial substance by weight, based on the total weight of the preparations, such as 0.001–40% w/w of the active compound, e.g. 0.1–20%, 0.5–10%, or 2–5%. More than one active substance may be incorporated in the composition. The composition is conveniently applied 1–10, such as 1, 2, 3 or 4 times a day, depending on the type, severity and localisation of the infection.

For topical application, the preparation may be formulated in accordance with conventional pharmaceutical practice with pharmaceutical excipients conventionally used for topical applications. The nature of the vehicle employed in the preparation of any particular composition will depend on the method intended for administration of that composition. Vehicles other than water that can be used in compositions and can include solids or liquids such as emollients, solvents, humectants, thickeners and powders. Examples of each of these types of vehicles, which can be used singly or as mixtures of one or more vehicles, are as follows:

- Emollients, such as stearyl alcohol, glyceryl monoricinoleate, glyceryl monostearate, propane-1,2-diol, butane-1,3-diol, cetyl alcohol, isopropyl isostearate, stearic acid, isobutyl palmitate, isocetyl stearate, oleyl alcohol, isopropyl laurate, hexyl laurate, decyl oleate, octadecan-2-ol, isocetyl alcohol, cetyl palmitate, dimethylpolysiloxane, di-n-butyl sebacate, isopropyl myristate, isopropyl palmitate, isopropyl stearate, butyl stearate, polyethylene glycol, triethylene glycol, lanolin, castor oil, acetylated lanolin alcohols, petroleum, mineral oil, butyl myristate, isostearic acid, palmitic acid, isopropyl linoleate, lauryl lactate, myristyl lactate, decyl oleate, myristyl myristate;
- solvents, such as water, methylene chloride, isopropanol, castor oil, ethylene glycol monoethyl ether, diethylene glycol monobutyl ether, diethylene glycol monoethyl ether, dimethyl sulfoxide, tetrahydrofuran, vegetable and animal oils, glycerol, ethanol, propanol, propylene glycol, and other glycols or alcohols, fixed oils;
- humectants or moistening agents, such as glycerin, sorbitol, sodium 2-pyrrolidone-5-carboxylate, soluble collagen, dibutyl phthalate, gelatin;
- powders, such as chalk, talc, kaolin, starch and derivatives thereof, gums, colloidal silicon dioxide, sodium polyacrylate, chemically modified magnesium aluminium silicate, hydrated aluminium silicate, carboxyvinyl polymer, sodium carboxymethyl cellulose, ethylene glycol monostearate;
- gelling or swelling agents, such as pectin, gelatin and derivatives thereof, cellulose derivatives such as methyl cellulose, carboxymethyl cellulose or oxidised cellulose, cellulose gum, guar gum, acacia gum, karaya gum, tragacanth gum, bentonite, agar, alginates, carbomer, gelatine, bladderwrack, ceratonia, dextran and derivatives thereof, ghatti gum, hectorite, ispaghula husk, xanthan gum;
- polymers, such as polylactic acid or polyglycolic acid polymers or copolymers thereof, paraffin, polyethylene, polyethylene oxide, polyethylene glycol, polypropylene glycol, polyvinylpyrrolidone;
- surfactants, such as non-ionic surfactants, e.g. glycol and glycerol esters, macrogol ethers and esters, sugar ethers and esters, such as sorbitan esters, ionic surfactants, such as amine soaps, metallic soaps, sulfated fatty alcohols, alkyl ether sulfates, sulfated oils, and ampholytic surfactants and lecitins;
- buffering agents, such as sodium, potassium, aluminium, magnesium or calcium salts (such as the chloride, carbonate, bicarbonate, citrate, gluconate, lactate, acetate, gluceptate or tartrate).

For topical application, the pH of the composition may in principle be within a very broad range such as 3–9. In a preferred embodiment of the invention, a pH close to physiological pH, e.g. a pH of about 4 to 8, is preferred. Conventional buffering agents as described above may be used to obtain the pH desired.

The preparation of the invention may also contain other additives such as stabilising agents, preservatives, solubilizers, colouring agents, chelating agents, gel forming agents, ointment bases, pH-regulators, anti-oxidants, perfumes and skin protective agents, etc. If the composition is in the form of a shampoo or soap, the composition may further comprise foaming agents, pearling agents and/or conditioners.

Typical preservatives include the parabens, formaldehyde, Kathon CG, Bronidox, Bronopol, p-chloro-m-cresol, chlorhexidine, benzalkonium chloride, etc.

Conventional ingredients may be used where the compositions of the invention are in the form of a shampoo or a soap, and typical soap and shampoo bases include such components as betaine, sodium lauryl sulphate, nonylphenol, imidazole, sulphosuccinate, refattening agents, humectants and conditioners.

Compositions may be formulated according to conventional pharmaceutical practice and may be: Semisolid formulations: Gels, pastes, mixtures. Liquid formulations: Solutions, suspensions, drenches, emulsions. As indicated, a pharmaceutical composition of the invention may comprise a substance of the invention, or a combination of such compounds. Examples of suitable functional derivatives include pharmaceutically acceptable salts, particularly those suitable for use in a cutaneous environment. Examples include pharmaceutically acceptable salts yielding anions which are pharmaceutically acceptable, particularly in a cutaneous environment. Examples include phosphates, sulphates, nitrate, iodide, bromide, chloride, borate as well as anions derived from carboxylic acids including acetate, benzoate, stearate, etc. Other derivatives of the amino function include amides, imides, ureas, carbamates, etc. Examples include salts with pharmaceutically acceptable cations, e.g. lithium, sodium, potassium, magnesium, calcium, zinc, aluminium, ferric, ferrous, ammonium and lower($C_1$–6)-alkylammonium salts. Esters include lower alkyl esters.

As will be understood by a person skilled in the art, peroral, parenteral, intravenous, topical, vaginal, or rectal formulations will follow the guidelines for topical application set forth above and according to conventional pharmaceutical practice, see, e.g., "Remington's Pharmaceutical Sciences" and "Encyclopedia of Pharmaceutical Technology".

The fourth step will be production of the substance of the invention with or without the presence of an antimicrobial under GMP, and submitting an application for clinical trials. These procedures are well described by the medical evaluation agencies and are known to a person skilled in the art.

The antimicrobial effect of the substance of the invention may be incorporated in diverse personal care and household product formulations, e.g. a preservative or as a disinfectant agent in accordance with standard practices. One embodiment of that finding will be the usage in cosmetics such as prevention and treatment of oily skin (acne). Another embodiment of that finding will be the usage for disinfection such as disinfection of surfaces, household utilities, industrial utilities, or contact lenses. Other potential applications include athlete's foot medication, sore throat, bad breath, or hand lotion for dry skin with small rashes or other areas of personal hygiene. Further applications include disinfection of dental utilities, dental implants, or dental prostheses. Potential formulations include shampoo, lotion, candies, ointment, tooth paste or foam spray and the formulations described above.

In a preferred embodiment of the present invention, the substance of the invention with or without an antimicrobial is used within the food industry for the preservation and/or disinfection of food in order to avoid food born infections.

One other important embodiment of the finding of the antimicrobial effect of the described substance will be the usage of the substance with or without the presence of an antimicrobial for combating microbial infections in plants. Plant pathogens exhibit a parasitic relationship in which the microorganism harms the host plant. Diseases in agricultural crops are immediate and cause long lasting damage. Out breaks of plant diseases destroy millions of acres of corps resulting in mass starvation especially in the undeveloped countries. The preferred plant pathogens to direct a composition with or without the presence of an antimicrobial including the substance described, are, but not limited to, Pseudomonas (e.g. *S. tabaci, S. angulata, S. phaseolicola, S. pisi, S. glycinea, S. syringae, S. solanacearum, S. caryophylli, S. cepacia, S. marginalis, S. savastonoi, S. marginata*), Xanthomonas (e.g. *X. phaseoli, X. oryzae, X. pruni, X. juglandis, X. campestris, X. vascularum*), Erwinia (e.g. *E. amylovora, E. tracheiphila, E. stewartii, E. carotovora*), Corynebacterium (e.g. *C. insidiosum, C. michiganese, C. facians*), Streptomyces (e.g. *S. scabies, S. ipomoeae*), Agrobacterium (e.g. *A. tumefaciens, A. rubi, A. rhizogenes*), Mycoplasma, or Sprioplasma, preferably against infections in tobacco, beans, peas, soybeans, lilac, banana, carnation, onion, olive, gladiolus, rice, fruits (e.g. pears, apples, peach), walnut, crucifers, citrus, sugar cane, curcurbits, corn, potato, chrysenthemum alfalfa, tomato, raspberries, or elm. The composition will be formulated and distributed according to methods known to the person skilled in the field.

REFERENCES

Cash, H. A. et al., 1979, Am. rev. Respir. Dis. 119, 453–459
Chatterjee, D. K. and Chakrabarty, A. M., 1982, Mol. Gen. Genet. 188:279–285.
Chen, P. S. et al 1956, Anal. Chem. 28:1756–1758.
Dutka-Malen, S. et al 1995, JCM 33:24–27
Gennis, R. B. 1989, In, Biomembranes: molecular structure and function, Springer-Verlag, New York.
Hancock, R. E. W., and Carey, A. M., 1979, J. Bacteriol. 140:902–910.
Hancock, R. E. W. ,1997, Trends in Microbiology 5:38–42.
Kernodle and Kaiser, 1994, Antimicrob, agents chemother. 38, 1325–1330.
Krivan, H. C., Franklin, D. P., Wang, W. T., Laux, D. C., and Cohen, P. S, 1992, Infect. Immun. 60:3943–3946.
Nikaido, H., 1996. In, F. C. Neidhardt (ed.), *Escherichia coli* and Salmonella, 2nd edition, ASM Press, Washington, D.C. pp. 29–47
Pace, J. et al. 1993, Cell 72:505–514.
Preston et al. 1 995, Infect. Immun. 63:3497–3501, 1995
Vaara, M. and Vaara, T., 1983, Antimicrob. Agents Chemother. 24:107–113.
Vaara, M., 1992, Microbiol.Rev. 56:395–411.
Viljanen, P. et al., 1991. Antibiot, J., 44:517–523.
Woodruff, W. A. and Hancock. R. E. W., 1988, J. Bacteriol. 170:2592–2598.
Zhou, X. et al. 1997. Appl. Environ. Microbiol. 63:1389–1395.

The invention will now be further illustrated by reference to certain specific examples which are provided herein for purposes of illustration only and are not intended to limit the scope therein.

EXAMPLES

Materials and Methods

Bacteria

*P. aeruginosa* PAO1 (Zhou, X. et al 1997) and *P. aeruginosa* AC869, a strain that degrades 3,5-dichlorobenzoate (Chatterjee, D. K., and Chakrabarty, A. M., 1982), were obtained from Dr. S. E. George from the National Health and Environmental Effects Research Laboratory, USEPA, Research Triangle Park, N.C. *P. aeruginosa* 9086-1 NMR, a non-mucoid revertant of a mucoid strain isolated from the sputum of a patient with cystic fibrosis and several mucoid antibiotic resistant strains of *P. aeruginosa*, isolated from the sputum of chronically infected cystic fibrosis patients, were obtained from Dr. G. Pier, Channing Laboratory, Harvard Medical School, Boston, Mass. *Pseudomonas aeruginosa* H103, a PAO1 strain (Hancock, R. E. W. and Carey, A. M., 1979) and H636, a protein F deficient strain derived from H103 (Woodruff, W. A., and Hancock, R. E. W., 1988), were obtained from Dr. R. E. W. Hancock, Department of Microbiology, University of British Columbia, Vancouver, British Columbia, Canada. *Pseudomonas aeruginosa* strains 17 AM, 47 AL, 77AM, 82 AM, 82 AM-NMR, PAO579, and 20 AL were obtained from Dr. G. Pier, Channing Laboratory, Harvard Medical School, Boston, Mass. *Pseudomonas aeruginosa* strains PAO579, 17107, and 19676 were obtained from Dr. Niels Hoiby, Danish Cystic Fibrosis Center, Department of Clinical Microbiology, Rigshospitalet, University of Copenhagen, Copenhagen, Denmark. *Pseudomonas aeruginosa* 82AM-NMR is a spontaneous non mucoid revertant of strain 82AM.

*Staphylococcus aureus*: MRSA #1, MRSA #2, MRSA #3, MRSA#988, MRSA #6052 were all obtained from the staphylococcus laboratory, (Statens Serum Institut, Artillerivej 5, 2300 Copenhagen, DENMARK).

*Enterococcus faecium* VRE BM 4147 van A, E. faecalis VRE V583 van B, E. gallinarum VRE BM 4174 van C-1 (as described in Dutka-Malen, S. et al., 1995) were obtained from Dutka-Malen.

*Klebsiella pneumoniae* clinical isolates were obtained from the Department of Microbiology (Statens Serum Institut, Artillerivej 5, 2300 Copenhagen, DENMARK).

All the bacterial strains were stored at −80° C. until further use.

Laboratory Media and Antibiotics

Luria-broth (L-broth) was prepared with 10 g Tryptone (Difco, Detroit, Mich.), 5 g NaCl, 5 g yeast extract (Difco, Detroit, Mich.) , 1 ml 1N NaOH in 1 l distilled $H_2O$. L-agar was prepared with L-broth containing 12% (w/v) Bacto-agar (DIFCO, Detroit, Mich.). Strains were grown at 37° C. in L-broth and plated on L-agar. Ampicillin, Piperacillin, and Methicillin were purchased from Sigma (St. Louis, Mo.). Ceftazidime (Glaxo-Welcome, UK) was obtained from a hospital pharmacy. All phospholipids were purchased from Avanti Polar-Lipids, Inc. (Alabaster, Ala.).

Procedure

Each of the tested phospholipids and the individual components in the phospholipids were tested at their concentrations present in DPPS at 1 mg/ml. Phospholipids were prepared by sonication into L-broth for 5 minutes in an ultrasonic water bath at room temperature and then incubated for 4 hours at 37° C. in a circulating water bath. At that time, any undissolved material was centrifuged out at 12,000×g for 10 minutes at 4° C., and the supernatants were used as the source of dissolved compound. The supernatants were then inoculated with the bacteria, and cultures were incubated with aeration for 18 h at 37° C. prior to plating on Luria-agar. Plates were incubated for 24 hours at 37° C. prior to counting.

Determination of MPPA Concentrations

To determine the amount of MPPA in suspension, MPPA supernatants (30 $\mu$L) and L-broth with no added MPPA (30 $\mu$L) were dissolved in 0.45 ml aliquots of 8.9N $H_2SO_4$ and heated at 210° C. for 25 minutes. After allowing samples to cool for 5 minutes, $H_2O_2$ (6 drops) was added to each sample, and samples were then heated at 210° C. for 30 minutes. Inorganic phosphorus released by this hydrolysis procedure was determined as described by Chen et al., 1956. In control experiments, essentially 100% of the inorganic phosphorus in known amounts of MPPA was detected by this method. The concentration of inorganic phosphorus in L-broth was subtracted from the total concentration of inorganic phosphorus in each MPPA supernatant to yield the concentration of MPPA inorganic phosphorus. All samples were run in triplicate. The concentration of MPPA in any supernatant was calculated based on the concentration of MPPA inorganic phosphorus in the supernatant and the percent of inorganic phosphorus by weight in MPPA. Supernatants made from MPPA suspensions at concentrations of 570 $\mu$g/ml, 1 mg/ml, and 2 mg/ml were assayed for phospholipid phosphate. The concentration of MPPA in each of the supernatants is shown in Table 1. For all concentrations, approximately 40 and 50% of the amounts were left in suspension.

Determination of cfu

The colony forming units (cfu) were determined by serial dilution and plating. Plates were incubated at 37° C. for 18 h and counted manually.

Measuring Calcium and Magnesium in L-Broth

Calcium concentrations were determined using a Beckman SYNCHRON EL-ISE Electrolyte System. This electrode simultaneously measures calcium, sodium, potassium, and chloride concentrations. Magnesium concentrations were determined using a Beckman SYNCHRON-CX-7 Autoanalyzer. The data are presented in Tables 21 and 22.

Example 1

Effect of Phospholipids on Gram Negative Bacteria

Effect of DPPS Against *Pseudomonas aeruginosa* PAO1

The MIC of ampicillin against *P. aeruginosa* PAO1 in L-broth is 2 mg/ml. A suspension of DPPS (1 mg/ml) was prepared as described previously and was inoculated with *P. aeruginosa* PAO1 ($5 \times 10^4$ cfu/ml). A second suspension of DPPS in L-broth containing 200 $\mu$g/ml of ampicillin was also inoculated with *P. aeruginosa* PAO1 in the same way. As controls, L-broth containing neither ampicillin nor DPPS and L-broth containing ampicillin (200 $\mu$g/ml) were inoculated with *P. aeruginosa* PAO1. As shown in Table 2, *P. aeruginosa* PAO1 grew to levels of about $10^{10}$ cfu/ml in L-broth, in L-broth containing DPPS in suspension, and in L-broth containing ampicillin. In contrast, *P. aeruginosa* PAO1 did not grow in L-broth containing both DPPS in suspension and ampicillin (Table 2). Therefore, DPPS in suspension appeared to be an enhancer of ampicillin activity against *P. aeruginosa* PAO1.

Effect of DPPS Against *Klebsiella pneumoniae*

The effect of DPPS in the antibiotic activity of ampicillin against *K. pneumoniae* was tested on 11 Klebsiella strains all clinical isolates with different MICs (range from 3 $\mu$g/ml to 128 $\mu$g/ml ampicillin). Growth of Klebsiella was monitored by CFU in L-broth with and without DPPS (1 mg/ml) adding serial dilutions of ampicillin concentrations (ranging from 0–1,024 $\mu$g/ml) depending on the strain's MIC. As control, L-broth without ampicillin and DPPS was used. For all 11 strains, the enhancement of antibiotic activity was confirmed. Representative results with the strain with the lowest MIC (3002) and the highest MIC (3024) are shown in Tables 3 and 4. As shown in Table 3 a *K. pneumoniae* strain relatively sensitive to ampicillin becomes even more sensitive when DPPS is added to the medium. Table 4 shows the effect even more profound in a strain relatively resistant to ampicillin.

Determination of the Optimal Structure of an Ampicillin Enhancer

Various components of DPPS were tested for their ability to enhance the activity of ampicillin (200 mg/ml) against *P. aeruginosa* PAO1. Each of the supernatants were made based on their weight in DPPS at 1 $\mu$g/ml. The compounds tested were dipalmitoylphosphatidic acid (DPPA, 0.88 mg/ml), which lacks the C3 serine, palmitic acid (PA, 0.68 mg/ml), dipalmitoylglycerol (DPG, 0.75 mg/ml), glycerol (0.12 mg/ml), glycerol-3-phosphate (G3P, 0.49 mg/ml), glycerophosphorylserine (GPS, 0.32 mg/ml), and phosphorylserine (PS, 0.2 mg/ml). As shown in Table 5, only DPPA had enhancing activity comparable to that seen previously using DPPS. Since no enhancing activity was observed with DPG, the importance of the phosphate was established. Moreover, since GPS had no enhancing activity, the importance of the fatty acids became clear. In support of this view, the only other compound that had any enhancing activity, although weak, was palmitic acid (Table 5).

Supernatants made from several other phospholipids were also tested for enhancing activity. The phospholipids tested were monomyristoylphosphatidic acid (MMPA, 0.53 mg/ml), which contains one myristic acid (C14) on C1 of the glycerol backbone, monopalmitoylphosphatidic acid (MPPA, 0.57 mg/ml), which contains one palmitic acid (C16) on C1 of the glycerol backbone, dilauroylphosphatidic acid (DLPA, 0.74 mg/ml), which contains one lauric acid (C12) on C1 and one lauric acid on C2 of the glycerol backbone, and dicaproylphosphatidic acid (DCPA, 0.51 mg/ml), which contains one caproic acid (C6) on C1 and one caproic acid on C2 of the glycerol backbone. The enhancing activities of MPPA and MMPA were greater than that of DPPA, which was greater than that of DPPS and DLPA, which had equal enhancing activities. DCPA, which is completely soluble in L-broth, had no enhancing activity (Table 6). Therefore, by removing the serine from DPPS to form DPPA, the enhancing activity of the phospholipid increased 100-fold and by additionally removing one palmitic acid from the C2 atom of the glycerol moiety of DPPA to form MPPA, the enhancing activity increased an additional 100-fold. Decreasing the chain length of the fatty acid in MPPA from a C16 backbone to a C14 backbone to form MMPA had no discernable effect on the ability to enhance ampicillin activity (Table 6). However, lowering fatty acid chain length from C16 in DPPA to C12 in DLPA decreased the ampicillin enhancing activity 100-fold and lowering it further to C6 to form DCPA abolished all enhancing activity (Table 6). Collectively, these results suggest that serine is not necessary for ampicillin enhancing activity in vitro, that lysophospholipids, i.e. phospholipids with only one fatty acid rather than two are more active enhancers than their parent phospholipids, and that phospholipids must have fatty acids with backbones of greater than 6 carbon atoms to enhance the activity of ampicillin.

Both DPPS and DPPA have net negative charges. To determine if net negative charge might be important for ampicillin enhancing activity, supernatants made using dipalmitoyl phosphatidylcholine (DPPC) and monopalmitoyl phophatidylcholine (MPPC) were tested for ampicillin enhancing activity against $P.$ $aeruginosa$ PAO1. Neither MPPC nor DPPC had any discernable ampicillin enhancing activity (Table 7), suggesting that the net negative charge on both DPPS and MPPA is important.

Determination of the Effect of Inocula on DPPS and MPPA Effect

Preincubated DPPS supernatant was inoculated with either $10^2$, $10^3$, $10^4$, $10^5$, or $10^6$ cfu/ml of $P.$ $aeruginosa$ PAO1 in the presence of 200 µg/ml of ampicillin and treated as described previously. The preincubated DPPS supernatant was effective in enhancing the activity of ampicillin up to an inoculum of $10^5$ cfu/ml, however, the inoculum of $10^6$ cfu/ml grew, slowly, in the presence of ampicillin (Table 8).

Preincubated supernatant, made using 570 µg/ml of MPPA in L-broth, was inoculated with either $5.3 \times 10^3$, $5.3 \times 10^4$, $5.3 \times 10^5$, $5.3 \times 10^6$, or $5.3 \times 10^7$ cfu/mlof $P.$ $aeruginosa$ PAO1 in the presence of 200 µg/ml of ampicillin and treated as described previously. The preincubated MPPA supernatant was effective in enhancing the activity of ampicillin to an inoculum of $5.3 \times 10^6$ cfu/ml (Table 9).

This indicates that there is a competition between the bacteria and the phospholipids for something in the medium, so that the more bacteria that are present, the more phospholipid is needed. This is not a problem since, as shown in Table 1, the more phospholipid added, the more stays in suspension. As will be shown in example 3, the bacteria and the phospholipids are competing for the calcium and magnesium present in L-broth.

Determination of MIC and MBC of Ampicillin in the Presence of MPPA

In this study, the minimum inhibitory concentration (MIC) is defined as the lowest concentration of the antimicrobial e.g. ampicillin that reduces growth by greater than one order of magnitude relative to the untreated culture and the minimum bactericidal concentration (MBC) as the lowest concentration of the antimicrobial e.g. ampicillin that results in an order of magnitude lower cfu/ml than at inoculation. Preincubated supernatant made using 570 µg/ml of MPPA in L-broth and containing ampicillin at concentrations of 10, 20, 40, 60, 80, 100 and 200 µg/ml, were inoculated with $P.$ $aeruginosa$ PAO1 ($3.5 \times 10^3$ cfu/ml) and tested for determination of MIC and MBC. The MBC, as judged by killing of the inoculum, was determined to be 40 µg/ml of ampicillin (Table 10) and the MIC, as determined by significant inhibition of growth was determined to be 20 µg/ml (Table 10). Therefore, MPPA lowered the MIC of ampicillin 100-fold, from 2 mg/ml to 20 µg/ml and lowered the MBC of ampicillin 100-fold, from 4 mg/ml to 40 µg/ml.

Effect of MPPA on Other $P.$ $aeruginosa$ Strains

Protein F appears to be the major porin of $P.$ $aeruginosa$, and it has been suggested that β-lactam antibiotics enter via protein F (Woodruff, W. A., and Hancock, R. E. W., 1988).

Protein F deficient mutants have MICs that are at most three times higher for β-lactam antibiotics than the wild-type parent. $P.$ $aeruginosa$ H636, a protein F deficient mutant, and its parent, $P.$ $aeruginosa$ H103 (Hancock, R. E. W., and Carey, A. M., 1979), were tested for MPPA enhancement of ampicillin activity. As shown in Table 1, H636 was more resistant to ampicillin (200 µg/ml) than its parent H103; however, in the presence of MPPA, ampicillin killed the entire H636 inoculum (Table 11). Therefore, it appears that MPPA does not require protein F to enhance the activity of ampicillin.

Effects of MPPA are also shown in the environmental isolate AC869 that degrades hydrocarbons. Four mucoid antibiotic resistant (ampicillin, carbenicillin, piperacillin, ciprofloxacin, etc) $P.$ $aeruginosa$ strains, recently isolated from the sputum of chronically infected cystic fibrosis patient (17 AM, 47 AL, 77 AM, 82 AM) were tested for MPPA enhanced sensitivity to ampicillin. Surprisingly, MPPA supernatants (570 µg/ml) inhibited growth of all four strains (Table 11). A non-mucoid revertant of one of the strains, (82 AM NMR), was also tested. MPPA inhibited the growth of 82 AM NMR as well (Table 11). MPPA did not enhance the activity of ampicillin on these strains (Table 11), which is not surprising since ampicillin is not active on non-growing bacteria. The PAO579, a cystic fibrosis strain, and the 9086-1 NMR, a non mucoid revertant of a cystic fibrosis strain, grew in the presence of MPPA, and were killed in the presence of MPPA and ampicillin as was the control strain PAO1 (Table 11).

MPPA Enhancement of Piperacillin and Ceftazidime

Since MPPA did not enhance the effects of ampicillin in cystic fibrosis strains that grow slowly in the presence of MPPA, the enhancing effect of MPPA on piperacillin activity (Table 12) was tested. MPPA enhanced the activity of piperacillin against all strains tested (Table 12). Essentially, the same results were observed with two additional cystic fibrosis strains using MPPA and ceftzadime (Table 13). Strains 17107 and 19676 are resistant to ceftazidime. MPPA also enhanced the activity of ceftazidime against those strains (Table 13).

Effect of MPPA on Growth

The $P.$ $aeruginosa$ strains 17 AM (Table 11), 47 AL (Table 11), 77AM (Table 11), 82 AM (Table 11), 82 AM-NMR (Table 11), 17107 (Table 13) were all inhibited in growth by the presence of MPPA without antibiotic. This indicates that MPPA might have bacteriostatic effect alone against certain Gram negative bacteria. The reason for this result is presently unknown; however it is known that the majority of $P.$ $aeruginosa$ strains isolated from cystic fibrosis patients have very little O-side chain on their lipopolysaccharide (LPS). Since MPPA competes with $P.$ $aeruginosa$ for calcium and magnesium (see example 3, below), and since LPS is stabilized in the $P.$ $aeruginosa$ outer membrane by divalent cations, it is possible that MPPA is more effective in competing for calcium and magnesium when the LPS on Gram negative bacteria is deficient in O-side chain.

Example 2

Effect of Phospholipids on Gram Positive Bacteria

MPPA Effect Against $S.$ $aureus$ with Antibiotics

Since many antibiotic resistant Gram positive bacteria are now the cause of many hospital acquired infections, MPPA was tested for methicillin enhancing activity against three methicillin resistant $Staphylococcus$ $aureus$ strains isolated from infected patients. Surprisingly, MPPA by itself killed all three strains (Table 14).

Effect of MPPA on Growth

The data in Table 15 also show that MPPA itself works as an antimicrobial. Both the methacillin resistant Staphylococcus and the vancomycin resistant Enterococcus are killed by the lipid although the medium provides good growth potential for the bacteria as seen by *S. aureus* grows up to $7.0 \times 10^9$ and Enterococcus up to $4.0 \times 10^8$.

Effect of DPG and DPPA on Growth

Other lipids, like DPG and DPPA had no effect on the Gram positive bacterial growth (Table 16) at the concentrations used. It could be speculated that higher doses should be used, or that only one fatty acid chain is required for the antimicrobial activity against Gram positive bacteria.

Effect of DPPC and MPPC on Growth

DPPC and MPPC were tested for antimicrobial activity against methycillin resistant *S. aureus* and vancomycin resistant *Enterococcus gallinarum*. In both cases, DPPC had no antimicrobial activity whereas MPPC killed both microorganisms (Tables 17 and 18). Of interest here is that both MPPA and MPPC are effective against Gram positive bacteria whereas only MPPA is active against Gram negative bacteria. As will be shown below, it appears that MPPA works on Gram negative bacteria by binding calcium and magnesium. MPPC would not be expected to bind these cations since it is not negatively charged. Yet MPPC does kill Gram positives. It therefor appears that phospholipids act on Gram negative and Gram positive bacteria via different mechanisms.

Example 3
Evidence of the Mechanism in Gram Negative Bacteria
Chelating Calcium and Magnesium Phospholipids are known to have affinity for calcium and magnesium (Gennis, R. B. 1989), and both have been suggested to be important for membrane stability. To determine whether MPPA might be binding calcium and, thereby, rendering PAO1 sensitive to ampicillin, several different experiments were performed. First, addition of calcium chloride (final concentrations of 200 μM and 400 μM) to MPPA (570 μg/ml) preincubated supernatants was performed. Whereas MPPA still enhanced ampicillin activity against *P. aeruginosa* PAO1 when the calcium concentration was increased by 200 μM, MPPA enhancement of ampicillin activity was lost when the calcium concentration was increased by 400 μM (Table 19). Second, addition of MPPA to a concentration of 2 mg/ml, incubated at 37° C. for 4 hours, centrifuged out any undissolved MPPA, and then addition of 400 μM calcium was carried out. Upon addition of the calcium, a visible white precipitate formed, suggesting that a calcium phospholipid complex had formed. Under these conditions, ampicillin activity against *P. aeruginosa* was still enhanced (Table 19).

Addition of magnesium did not reverse MPPA enhancement of ampicillin activity to the same extent as calcium (Table 20). That is, *P. aeruginosa* was still killed in the presence of MPPA, ampicillin, and an additional 200 μM magnesium, and did not grow in the presence of MPPA, ampicillin and an additional 400 μM magnesium (Table 20). The data in Table 20 suggest that MPPA binds both calcium and magnesium and thereby destabilizes the *P. aeruginosa* outer membrane (reviewed in Hancock, R. E W. 1997, Nikaido, H. 1996, and Vaara, M. 1992). In support of this view, when calcium and magnesium concentrations were determined in MPPA supernatants, it was found that MPPA reduces the concentration of calcium 4–5 (Table 21) fold and of magnesium between 10 and 20 fold (Table 22), depending on the concentration of MPPA in the supernatant.

Example 4
Effect of MPPA Against Corneal Infections in Mice

Corneal infections in mice were carried out using the model described by Preston et al 1995. Briefly, CD-1 male mice, purchased from Charles River Breeding laboratories (Wilmington, Mass.) were given intraperitoneal injections of 0.2 ml containing 6.7 mg of ketamine hydrochloride and 1.3 mg of xylazine. After the mice were anaesthetized, three 1 mm-long scratches were made in the corneal epithelium and superficial stroma of each mouse with a 27-gauge needle. An overnight 37° C. L-broth grown culture of *P. aeruginosa* PAO1 that had been washed in fresh L-broth to remove extracellular products was used to infect mice. Each mouse was immediately inoculated in the scratched eye with $5 \times 10^7$ cfu of *P. aeruginosa* PAO1 (5 μL of culture at $1 \times 10^{10}$ cfu/ml). Thirty minutes later, the scratched eyes of one set of mice were washed with 5 μL of sterile L-broth, the scratched eyes of a second set of mice were washed with 5 μL of sterile broth containing MPPA (570 μg/ml supernatant), the scratched eyes of a third set of mice were washed with 5 μL of sterile L-broth containing ampicillin (500 μg/ml), and the scratched eyes of a fourth set of mice were washed with 5 μL of sterile L-broth containing MPPA (570 μg/ml supernatant) and ampicillin (500 μg/ml). The washing procedure was repeated twice at 5 hour intervals and the entire series of 3 washes per day were repeated for 4 days at which time the mice were scored for infection by corneal opacity. As shown in Table 23, washing with MPPA and ampicillin resulted in fewer eye infections than washing with either compound alone or with sterile L-broth.

TABLES

TABLE 1

MPPA concentration in MPPA supernatants.

| Experiment number | MPPA added (μg/ml) | MPPA in supernatant μg/ml ± SD (mM) |
|---|---|---|
| 1 | 570 | 241 ± 72 (0.56) |
| 2 | 570 | 260 ± 24 (0.60) |
| 1 | 1000 | 415 ± 82 (0.96) |
| 2 | 1000 | 384 ± 42 (0.89) |
| 2 | 2000 | 1290 ± 117 (3.0) |

TABLE 2

Enhancement of ampicillin activity against *P. aeruginosa* PAO1 by DPPS.

| DPPS 1 mg/ml | Ampicillin 200 μg/ml | PAO1 18 hr |
|---|---|---|
| − | − | $9.7 \times 10^9$ |
| + | − | $1.2 \times 10^{10}$ |
| − | + | $4.4 \times 10^9$ |
| + | + | $1.2 \times 10^5$ |

Inoculum $5 \times 10^4$ cfu/ml

TABLE 3

DPPS enhancement of ampicillin against Klebsiella pneumonia 3002

| DPPS 1 mg/ml | Ampicillin (μg/ml) | 18 hour cfu/ml |
|---|---|---|
| − | 0 | $1.8 \times 10^9$ |
| + | 0 | $1.3 \times 10^9$ |
| − | 4 | $1.7 \times 10^9$ |
| + | 4 | $5.0 \times 10^8$ |
| − | 8 | $5.0 \times 10^8$ |
| + | 8 | $1.1 \times 10^8$ |
| − | 16 | $2.3 \times 10^8$ |
| + | 16 | $1.5 \times 10^3$ |
| − | 32 | $<10^3$ |
| + | 32 | $<10^3$ |

Inoculum $3.0 \times 10^4$ cfu/ml.

TABLE 4

DPPS enhancement of ampicillin against Klebsiella pneumonia 3024

| DPPS 1 mg/ml | Ampicillin (μg/ml) | 18 hour cfu/ml |
|---|---|---|
| − | 0 | $1.7 \times 10^9$ |
| + | 0 | $1.5 \times 10^9$ |
| − | 16 | $1.6 \times 10^9$ |
| + | 16 | $1.7 \times 10^9$ |
| − | 32 | $1.1 \times 10^9$ |
| + | 32 | $4.5 \times 10^8$ |
| − | 64 | $1.8 \times 10^8$ |
| + | 64 | $1.2 \times 10^3$ |
| − | 128 | $1.9 \times 10^6$ |
| + | 128 | $<10^3$ |
| − | 256 | $<10^3$ |
| + | 256 | $<10^3$ |

Inoculum $4.5 \times 10^4$ cfu/ml.

TABLE 5

Enhancing activities against P. aeruginosa PAO1 by various phospholipids.

| Compound (Concentration (mg/ml)) | Structure | Ampicillin 200 μg/ml | PAO1 18 hr |
|---|---|---|---|
| none | | + | $1.1 \times 10^{10}$ |
| DPPS | C16-C | − | $1.3 \times 10^{10}$ |
| (1.0) | C16-C | + | $1.8 \times 10^2$ |
|  | C-P-Serine | | |
| DPPA | C16-C | − | $9.1 \times 10^9$ |
| (0.88) | C16-C | + | <10 |
|  | C-P | | |
| PA | C16 | − | $1.5 \times 10^{10}$ |
| (0.68) |  | + | $1.2 \times 10^6$ |
| DPG | C16-C | − | $6.3 \times 10^9$ |
| (0.75) | C | + | $7.2 \times 10^9$ |
|  | C16-C | | |
| Glycerol | C | − | $1.0 \times 10^{10}$ |
| (0.12) | C | + | $9.2 \times 10^9$ |
|  | C | | |
| G3P | C | − | $1.8 \times 10^{10}$ |
| (0.49) | C | + | $9.2 \times 10^9$ |
|  | C-P | | |
| GPS | C | − | $1.2 \times 10^{10}$ |
| (0.32) | C | + | $9.5 \times 10^9$ |
|  | C-P-Serine | | |
| PS | P-Serine | − | $1.3 \times 10^{10}$ |
| (0.2) |  | + | $7.9 \times 10^9$ |

Inoculum $4.4 \times 10^3$ cfu/ml.

TABLE 6

Enhancing activities against P. aeruginosa PAO1 by various phospholipids.

| Compound (Concentration (mg/ml)) | Structure | Ampicillin 200 μg/ml | PAO1 18 hr |
|---|---|---|---|
| NONE |  | + | $3.4 \times 10^9$ |
| DPPS | C16-C | − | $4.7 \times 10^9$ |
| (1.0) | C16-C | + | $2.0 \times 10^4$ |
|  | C-P-Serine | | |
| DPPA | C16-C | − | $7.1 \times 10^9$ |
| (0.88) | C16-C | + | $2.0 \times 10^2$ |
|  | C-P | | |
| MMPA | C14-C | − | $5.2 \times 10^9$ |
| (0.53) | C | + | <10 |
|  | C-P | | |

TABLE 6-continued

Enhancing activities against P. aeruginosa PAO1 by various phospholipids.

| Compound (Concentration (mg/ml)) | Structure | Ampicillin 200 μg/ml | PAO1 18 hr |
|---|---|---|---|
| MPPA | C16-C | − | $2.6 \times 10^9$ |
| (0.57) | C | + | <10 |
|  | C-P | | |
| DLPA | C12-C | − | $2.8 \times 10^9$ |
| (0.74) | C12-C | + | $2.2 \times 10^4$ |
|  | C-P | | |
| DCPA | C6-C | − | $1.4 \times 10^{10}$ |
| (0.51) | C6-C | + | $7.1 \times 10^9$ |
|  | C-P | | |

Inoculum $6.4 \times 10^3$ cfu/ml.

TABLE 7

Enhancing activities against P. aeruginosa PAO1 by various phospholipids

| Phospholipid (concentration (μg/ml)) | Ampicillin (200 μg/ml) | 18 hour cfu/ml (percent survival) |
|---|---|---|
| None | − | $1.4 \times 10^{10}$ |
| None | + | $9.8 \times 10^9$ |
| MPPA | − | $4.5 \times 10^9$ |
| (570) | + | <10 |
| DPPC | − | $1.7 \times 10^{10}$ |
| (1000) | + | $1.4 \times 10^{10}$ |
| MPPC | − | $1.6 \times 10^{10}$ |
| (675) | + | $1.5 \times 10^{10}$ |

Inoculum $8.8 \times 10^4$ cfu/ml.

TABLE 8

DPPS enhancement of ampicillin activity at various inocula of P. aeruginosa PAO1.

| Input cfu/ml | 18 hr cfu/ml | 18 hr cfu/input cfu |
|---|---|---|
| $1.3 \times 10^3$ (No ampicillin) | $4.2 \times 10^9$ | 3200000 |
| $1.3 \times 10^2$ | <10 | <0.077 |
| $1.3 \times 10^3$ | $2.5 \times 10^3$ | 1.92 |
| $1.3 \times 10^4$ | $1.0 \times 10^3$ | 0.077 |
| $1.3 \times 10^5$ | $7.6 \times 10^3$ | 0.059 |
| $1.3 \times 10^6$ | $3.5 \times 10^8$ | 269 |

Concentration of DPPS was 1 mg/ml.
Concentration of ampicillin was 200 μg/ml.

TABLE 9

MPPA enhancement of ampicillin activity at various inocula of P. aeruginosa PAO1.

| Input cfu/ml | 18 hr cfu/ml | 18 hr cfu/input cfu |
|---|---|---|
| $5.3 \times 10^3$ (No ampicillin) | $3.1 \times 10^9$ | 580000 |
| $5.3 \times 10^3$ | 10 | 0.0019 |
| $5.3 \times 10^4$ | <10 | <0.00019 |
| $5.3 \times 10^5$ | $4.4 \times 10^2$ | 0.00083 |
| $5.3 \times 10^6$ | $1.7 \times 10^2$ | 0.000032 |
| $5.3 \times 10^7$ | $1.3 \times 10^6$ | 0.025 |

Concentration of MPPA was 570 μg/ml.
Concentration of ampicillin was 200 μg/ml.

TABLE 10

MIC and MBC of ampicillin against *P. aeruginosa* PAO1 in the presence of MPPA.

| MPPA 570 μg/ml | Ampicillin (μg/ml) | 18 hour cfu/ml |
|---|---|---|
| − | 200 | $9.8 \times 10^9$ |
| + | 0 | $3.3 \times 10^9$ |
| + | 10 | $6.0 \times 10^8$ |
| + | 20 | $7.7 \times 10^5$ MIC |
| + | 40 | $4.4 \times 10^2$ MBC |
| + | 60 | 60 |
| + | 80 | 40 |
| + | 100 | <10 |
| + | 200 | <10 |

Inoculum $3.5 \times 10^3$ cfu/ml.

TABLE 11

MPPA enhancement of ampicillin activity against various *P. aeruginosa* strains.

| Strain (Inoculum (cfu/ml)) | MPPA (570 μg/ml) | Ampicillin (200 μg/ml) | 18 hr cfu/ml |
|---|---|---|---|
| H103 ($1.1 \times 10^4$ cfu/ml) | − | − | $5.6 \times 10^9$ |
| | + | − | $4.3 \times 10^9$ |
| | − | + | $1.2 \times 10^7$ |
| | + | + | <10 |
| H636 ($1.4 \times 10^4$ cfu/ml) | − | − | $2.0 \times 10^9$ |
| | + | − | $5.1 \times 10^9$ |
| | − | + | $9.5 \times 10^8$ |
| | + | + | <10 |
| PAO1 ($6.0 \times 10^3$ cfu/ml) | − | + | $2.5 \times 10^9$ |
| | + | − | $5.5 \times 10^9$ |
| | + | + | <10 |
| AC869 ($5.0 \times 10^3$ cfu/ml) | − | + | $5.5 \times 10^9$ |
| | + | − | $5.6 \times 10^9$ |
| | + | + | 10 |
| 9086-1 NMR ($5.5 \times 10^3$ cfu/ml) | − | + | $5.8 \times 10^9$ |
| | + | − | $2.1 \times 10^9$ |
| | + | + | $2.4 \times 10^2$ |
| H103 ($1.1 \times 10^4$ cfu/ml) | − | + | $1.2 \times 10^7$ |
| | + | − | $4.3 \times 10^9$ |
| | + | + | <10 |
| 17 AM ($2.0 \times 10^3$ cfu/ml) | − | − | $4.9 \times 10^9$ |
| | + | − | $9.6 \times 10^2$ |
| | + | + | $1.6 \times 10^3$ |
| 47 AL ($1.1 \times 10^3$ cfu/ml) | − | − | $2.2 \times 10^9$ |
| | + | − | $4.8 \times 10^2$ |
| | + | + | $3.0 \times 10^1$ |
| 77 AM ($1.7 \times 10^3$ cfu/ml) | − | − | $9.7 \times 10^9$ |
| | + | − | $1.4 \times 10^2$ |
| | + | + | $3.0 \times 10^1$ |
| 82 AM ($1.0 \times 10^3$ cfu/ml) | − | − | $1.2 \times 10^{10}$ |
| | + | − | $6.9 \times 10^2$ |
| | + | + | $3.4 \times 10^3$ |
| 82 AM-NMR ($1.0 \times 10^3$ cfu/ml) | − | − | $6.5 \times 10^7$ |
| | + | − | $6.1 \times 10^2$ |
| | + | + | $1.4 \times 10^3$ |
| PA0579 ($1.3 \times 10^3$ cfu/ml) | − | − | $3.8 \times 10^9$ |
| | − | + | $1.8 \times 10^9$ |
| | + | − | $5.8 \times 10^8$ |
| | + | + | <10 |
| PAO1 ($5.0 \times 10^3$ cfu/ml) | − | − | $1.4 \times 10^{10}$ |
| | + | − | $1.1 \times 10^{10}$ |
| | + | + | <10 |

TABLE 12

MPPA enhancement of piperacillin activity against various strains of *P. aeruginosa*.

| Strain (Inoculum (cfu/ml)) | MPPA 570 μg/ml | Piperacillin 50 μg/ml | 18 hr cfu/ml |
|---|---|---|---|
| 17 AM ($5.8 \times 10^3$ cfu/ml) | + | − | $7.3 \times 10^5$ |
| | − | + | $9.0 \times 10^6$ |
| | + | + | $2.3 \times 10^2$ |
| 20 AL ($3.6 \times 10^3$ cfu/ml) | + | − | $6.6 \times 10^6$ |
| | − | + | $1.4 \times 10^4$ |
| | + | + | $1.2 \times 10^2$ |
| 77AM ($2.1 \times 10^3$ cfu/ml) | + | − | $5.8 \times 10^4$ |
| | − | + | $9.6 \times 10^6$ |
| | + | + | <10 |
| 82 AM ($3.1 \times 10^3$ cfu/ml) | + | − | $2.1 \times 10^6$ |
| | − | + | $1.7 \times 10^5$ |
| | + | + | <10 |
| 82 AM-NMR ($3.1 \times 10^3$ cfu/ml) | + | − | $3.4 \times 10^3$ |
| | − | + | $2.5 \times 10^6$ |
| | + | + | <10 |

TABLE 13

MPPA enhancement of ceftazidime activity against various *P. aeruginosa* strains.

| Strain (Inoculum (cfu/ml)) | MPPA (570 μg/ml) | Ceftazidime (100 μg/ml) | cfu/ml |
|---|---|---|---|
| 17107 ($3.5 \times 10^2$ cfu/ml) | − | − | $1.0 \times 10^8$ |
| | − | + | $2.2 \times 10^5$ |
| | + | − | $2.0 \times 10^4$ |
| | + | + | <10 |
| 19676 ($2.8 \times 10^3$ cfu/ml) | − | − | $1.9 \times 10^{10}$ |
| | − | + | $2.3 \times 10^3$ |
| | + | − | $3.5 \times 10^8$ |
| | + | + | <10 |

TABLE 14

MPPA effect on *S. aureus*

| Strain (Inoculum (cfu/ml)) | MPPA (570 μg/ml) | Methicillin μg/ml | cfu/ml |
|---|---|---|---|
| MRSA#1 ($4.4 \times 10^3$ cfu/ml) | − | − | $5.0 \times 10^9$ |
| | − | 20 | $1.2 \times 10^9$ |
| | − | 40 | $4.1 \times 10^9$ |
| | + | − | <10 |
| | + | 20 | <10 |
| | + | 40 | <10 |
| MRSA#2 ($3.3 \times 10^3$ cfu/ml) | − | − | $8.0 \times 10^9$ |
| | − | 20 | $1.5 \times 10^9$ |
| | − | 40 | $3.8 \times 10^9$ |
| | + | − | <10 |
| | + | 20 | <10 |
| | + | 40 | <10 |
| MRSA#3 $3.3 \times 10^3$ cfu/ml | − | − | $8.0 \times 10^9$ |
| | − | 20 | $1.5 \times 10^9$ |
| | − | 40 | $3.8 \times 10^9$ |
| | + | − | <10 |
| | + | 20 | <10 |
| | + | 40 | <10 |

TABLE 15

MPPA effect on *S. aureus* and Enterococcus

| Strain (Inoculum (cfu/ml)) | MPPA 570 μg/ml | cfu/ml |
|---|---|---|
| MRSA#1 | − | $3.3 \times 10^9$ |
| ($8.9 \times 10^3$ cfu/ml) | + | <10 |
| MRSA#3 | − | $2.2 \times 10^9$ |
| ($4.8 \times 10^3$ cfu/ml) | + | <10 |
| MRSA#988 | − | $4.6 \times 10^9$ |
| ($8.4 \times 10^3$ cfu/ml) | + | <10 |
| MRSA#6052 | − | $8.4 \times 10^9$ |
| ($6.7 \times 10^3$ cfu/ml) | + | $4 \times 10^1$ |
| VRE BM 4147 van A | − | $1.6 \times 10^8$ |
| ($8.6 \times 10^2$ cfu/ml) | + | <10 |
| VRE V583 van B | − | $4.6 \times 10^8$ |
| ($1.5 \times 10^3$ cfu/ml) | + | $1.8 \times 10^2$ |
| VRE BM 4174 van C-1 | − | $6.0 \times 10^8$ |
| ($6.2 \times 10^2$ cfu/ml) | + | <10 |

TABLE 16

DPG and DPPA effect on *S. aureus* and Enterococcus

| Strain (Inoculum (cfu/ml)) | DPG 750 μg/ml | DPPA 880 μg/ml | cfu/ml |
|---|---|---|---|
| MRSA#3 | − | − | $7.5 \times 10^9$ |
| $5.0 \times 10^3$ cfu/ml | + | − | $9.8 \times 10^9$ |
|  | − | + | $4.4 \times 10^9$ |
| MRSA#988 | − | − | $4.2 \times 10^9$ |
| $7.1 \times 10^3$ cfu/ml | + | − | $1.4 \times 10^{10}$ |
|  | − | + | $7.6 \times 10^9$ |
| MRSA#6052 | − | − | $4.7 \times 10^9$ |
| $5.1 \times 10^3$ cfu/ml | + | − | $1.4 \times 10^{10}$ |
|  | − | + | $6.0 \times 10^9$ |
| VRE BM 4147 vanA | − | − | $2.1 \times 10^8$ |
| $1.1 \times 10^3$ cfu/ml | + | − | $4.2 \times 10^9$ |
|  | − | + | $4.5 \times 10^7$ |
| VRE V583 vanB | − | − | $1.1 \times 10^8$ |
| $5.1 \times 10^3$ cfu/ml | + | − | $4.2 \times 10^8$ |
|  | − | + | $2.9 \times 10^8$ |
| VRE BM 4174 van C-1 | − | − | $1.5 \times 10^8$ |
| $1.2 \times 10^2$ cfu/ml | + | − | $3.1 \times 10^8$ |
|  | − | + | $3.4 \times 10^8$ |

TABLE 17

Effect of DPPC and MPPC on growth of *S. aureus* MRSA#988

| Phospholipid (Concentration (mg/ml)) | 18 hour cfu/ml |
|---|---|
| None | $7.6 \times 10^9$ |
| DPPC (1000) | $6.6 \times 10^9$ |
| MPPC (675) | $4.0 \times 10^1$ |

Inoculum $5.0 \times 10^4$ cfu/ml

TABLE 18

Effect of DPPC and MPPC on growth of *Enterococcus gallinarum* VRE MB4174 van C-1

| Phospholipid (Concentration (mg/ml)) | 18 hour cfu/ml |
|---|---|
| None | $5.8 \times 10^8$ |
| DPPC (1000) | $1.1 \times 10^9$ |
| MPPC (675) | <10 |

Inoculum $1.8 \times 10^3$ cfu/ml

TABLE 19

MPPA enhancement of ampicillin activity against *P. aeruginosa* with added Ca ++.

| MPPA (μg/ml) | Ca ++ added (μM) | Ampicillin (μg/ml) | cfu/ml[a] |
|---|---|---|---|
| 570 | none | none | $5.3 \times 10^9$ |
| 570 | none | 200 | <10 |
| 570 | 200 | none | $2.1 \times 10^9$ |
| 570 | 200 | 200 | $1.3 \times 10^3$ |
| 570 | 400 | none | $4.9 \times 10^9$ |
| 570 | 400 | 200 | $5.5 \times 10^9$ |
| 2000 | 400b | none | $3.3 \times 10^9$ |
| 2000 | 400b | 200 | <10 |

[a]Cultures were inoculated at $1.5 \times 10^4$ cfu/ml
[b]Calcium chloride (400 μM) was added to the 2 mg/ml supernatant. A second precipitate formed which was removed by centrifugation prior to inoculation.

TABLE 20

MPPA enhancement of ampicillin activity against *P. aeruginosa* with added Mg ++.

| MPPA (μg/ml) | Mg ++ added (μM)[a] | Ampicillin (μg/ml) | cfu/ml[b] |
|---|---|---|---|
| none | none | 200 | $3.9 \times 10^9$ |
| 570 | none | none | $8.1 \times 10^9$ |
| 570 | none | 200 | <10 |
| 570 | 200 | 200 | <10 |
| none | 400 | 200 | $1.1 \times 10^9$ |
| 570 | 400 | 200 | $8.6 \times 10^3$ |

[a]Magnesium was added as magnesium chloride.
[b]Cultures were inoculated at $3.1 \times 10^3$ cfu/ml.

TABLE 21

Calcium concentrations in supernatants of L-broth containing MPPA.

| Ca++ added (μM) | MPPA added (mg/ml) | Ca++ remaining (μM)[a] |
|---|---|---|
| none | none | 263 |
| none | 0.10 | 73 |
| none | 0.57 | 73 |
| none | 2.0 | 55 |
| 400 | none | 700 |
| 400 | 2.0 | 55 |

[a]Ca ++ remaining after centrifugation. Total Ca ++ was measured using a Beckman SYNCHRON EL-ISE Electrolyte System. Sodium, potassium and chloride concentrations remained constant at 103 mM, 7.5 mM, and 94 mM respectively.

TABLE 22

Magnesium concentrations in supernatants of LB containing MPPA.

| MPPA added (mg/ml) | Mg ++ remaining (μM)[a] |
|---|---|
| none | 225 |
| 0.10 | 200 |
| 0.57 | 29 |
| 2.0 | 13 |

[a]Mg ++ remaining after centrifugation. Total Mg ++ was measured using a Beckman SYNCRON-CX-7 Autoanalyzer.

TABLE 23

Effect of MPPA on mouse eye infection with *P. aeruginosa* PAO1.

| Treatment | #Infected/#Inoculated |
|---|---|
| None | 6/6 |
| Ampicillin | 6/6 |
| MPPA | 4/6 |
| MPPA + Ampicillin | 3/6 |

MPPA concentration 570 ug/ml
Ampicillin concentration 500 μg/ml.

Mice were scored for infection 4 days after inoculation. A mouse was considered to be infected if the eye appeared opaque relative to the normal eye.

What is claimed is:

1. An antimicrobial composition substance comprising
a) at least one substance of the formula (I):

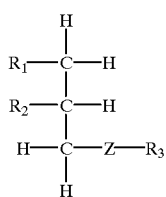

(I)

wherein:
Z represents a phosphorus or sulfur oxyacid residue;
one of $R_1$ and $R_2$ represents a hydroxy group and the other of $R_1$ and $R_2$ represents a saturated or unsaturated fatty acid residue with at least 7 carbon atoms; and
$R_3$ represents a hydrogen; and
b) at least one antimicrobial.

2. The composition according to claim 1, wherein the antimicrobial is selected from the group consisting of: β-lactams, vancomycin and second generation drugs thereof, monobactams, tetracyclines, chloramphenicol, aminoglycosides, polymyxins, erythromycins, lincomycins, sulfonamides, trimethroprim, quinolones, novobiocin, pyrimethamine and rifampin.

3. The composition according to claim 1 or 2, wherein Z is

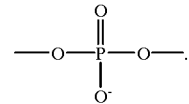

4. The composition according to claim 3, wherein $R_1$ or $R_2$ is a fatty acid residue with 12, 13, 14, 15, or 16 carbon atoms.

5. The composition according to claim 3, wherein $R_2$ represents a hydroxy group.

6. The composition of claim 1, wherein said substance is formulated as a paste.

7. The composition of claim 1, wherein said composition is in the form of a liquid.

8. The method of claim 1, wherein said composition is in the form of a vapor.

9. A method of treatment comprising administering to an animal with a bacterial infection an antibacterial amount of the composition of claim 1 or 2.

10. The method of claim 6, where in said infection is associated with wound burns, ulcus cruris, or acne.

11. The method of claim 6, wherein said infection is associated with eye infection, periodontitis, otitis, mouth infection, or throat infection.

12. The method of claim 6, wherein said infection is associated with lung infection.

13. The method of claim 6, wherein said animal is a mammal.

14. The method of claim 6, wherein said animal is a human being.

15. The method of claim 6, wherein said animal is a farm animal.

* * * * *

UNITED STATES PATENT AND TRADEMARK OFFICE
CERTIFICATE OF CORRECTION

PATENT NO. : 6,165,997
DATED : December 26, 2000
INVENTOR(S) : Cohen et al.

It is certified that error appears in the above-identified patent and that said Letters Patent is hereby corrected as shown below:

Column 23,
Line 35, under "cfu/ml", delete "$10^9$" and insert -- $10^8$ --.

Signed and Sealed this

Seventh Day of September, 2004

JON W. DUDAS
*Director of the United States Patent and Trademark Office*